US009872754B2

(12) United States Patent
Tuechsen et al.

(10) Patent No.: US 9,872,754 B2
(45) Date of Patent: Jan. 23, 2018

(54) ORTHOPEDIC PACKAGING

(71) Applicant: Stryker European Holdings I, LLC, Kalamazoo, MI (US)

(72) Inventors: Inka Tuechsen, Gelting (DE); Christian Heizmann, Langendorf (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/854,477

(22) Filed: Sep. 15, 2015

(65) Prior Publication Data

US 2016/0074118 A1 Mar. 17, 2016

Related U.S. Application Data

(60) Provisional application No. 62/050,407, filed on Sep. 15, 2014.

(51) Int. Cl.
| *A61F 2/00* | (2006.01) |
| *A61B 17/86* | (2006.01) |
| *A61B 19/02* | (2006.01) |
| *B65B 69/00* | (2006.01) |
| *B65D 77/04* | (2006.01) |

(Continued)

(52) U.S. Cl.
CPC .......... *A61F 2/0095* (2013.01); *A61B 17/865* (2013.01); *A61B 19/026* (2013.01); *A61B 50/20* (2016.02); *A61B 50/30* (2016.02); *B65B 69/005* (2013.01); *B65D 77/0446* (2013.01); *B65D 77/30* (2013.01); *A61B 2050/005* (2016.02); *A61B 2050/0065* (2016.02); *B65D 2577/2041* (2013.01)

(58) Field of Classification Search
CPC ....... A61B 17/00; A61B 17/80; A61B 17/865; A61B 17/88; A61B 19/00; A61B 19/02; A61B 19/026; A61B 50/20; A61B 50/30; A61B 77/04; A61B 77/0446; A61B 77/30; A61B 2577/2041; A61B 17/06; A61F 2/00; A61F 2/0095; B65B 69/00; B65B 69/005; B65D 83/10; B65D 77/04; B65D 77/0446; B65D 77/30; B65D 2577/2041

USPC ................ 206/363–370, 438, 439, 461–471, 206/570–572; 53/492

See application file for complete search history.

(56) References Cited

U.S. PATENT DOCUMENTS

| 4,856,648 A | 8/1989 | Krueger |
| 5,193,679 A * | 3/1993 | White .................... A61F 2/0095 |
| | | 206/363 |

(Continued)

FOREIGN PATENT DOCUMENTS

| FR | 2854143 A1 | 10/2004 |
| FR | 2876086 A1 | 4/2006 |

(Continued)

OTHER PUBLICATIONS

Extended European Search Report for Application No. 15185241.5 dated Jan. 15, 2016.
Stryker Trauma GmbH, Gamma nail blister packaging Implant, 2008.

*Primary Examiner* — Bryon Gehman
(74) *Attorney, Agent, or Firm* — Lerner, David, Littenberg, Krumholz & Mentlik, LLP

(57) ABSTRACT

A package for an orthopedic device is disclosed. The package includes inner and outer packaging and preferably allows for accessibility of the orthopedic device without direct handling by hand. Methods of utilizing such packaging are also disclosed.

17 Claims, 12 Drawing Sheets

(51) Int. Cl.
  *B65D 77/30* (2006.01)
  *A61B 50/20* (2016.01)
  *A61B 50/30* (2016.01)
  *A61B 50/00* (2016.01)

(56) References Cited

U.S. PATENT DOCUMENTS

| | | | | |
|---|---|---|---|---|
| 5,405,005 A | * | 4/1995 | White | A61F 2/0095 |
| | | | | 206/363 |
| 5,494,162 A | * | 2/1996 | Treace | A61F 2/0095 |
| | | | | 206/438 |
| 5,669,501 A | * | 9/1997 | Hissong | A61F 2/0095 |
| | | | | 206/363 |
| 5,772,031 A | | 6/1998 | Landis | |
| 6,254,294 B1 | * | 7/2001 | Muhar | A61M 35/006 |
| | | | | 206/572 |
| 7,451,870 B2 | * | 11/2008 | Donahoe | A61C 8/0087 |
| | | | | 206/63.5 |
| 8,069,980 B2 | * | 12/2011 | Stopek | A61B 17/06133 |
| | | | | 206/363 |
| 8,413,811 B1 | * | 4/2013 | Arendt | A61C 8/0087 |
| | | | | 206/365 |
| 8,985,331 B2 | * | 3/2015 | Guenter | A61C 8/0087 |
| | | | | 206/438 |
| 9,265,579 B2 | * | 2/2016 | Richart | A61B 17/865 |
| 9,371,156 B2 | * | 6/2016 | Moir | B65D 43/22 |
| 9,414,893 B2 | * | 8/2016 | Jacobson | A61B 50/30 |
| 2004/0112781 A1 | * | 6/2004 | Hofverberg | B65D 25/10 |
| | | | | 206/438 |
| 2005/0033430 A1 | | 2/2005 | Powers et al. | |
| 2007/0295620 A1 | * | 12/2007 | Collet | A61C 8/0087 |
| | | | | 206/63.5 |
| 2014/0042050 A1 | | 2/2014 | Richart et al. | |
| 2015/0142073 A1 | * | 5/2015 | Taff | B65B 55/02 |
| | | | | 206/570 |

FOREIGN PATENT DOCUMENTS

| | | |
|---|---|---|
| FR | 2974290 A1 | 10/2012 |
| GB | 2391852 A | 2/2004 |
| TW | 201231359 A | 8/2012 |
| WO | 03079918 A1 | 10/2003 |

* cited by examiner

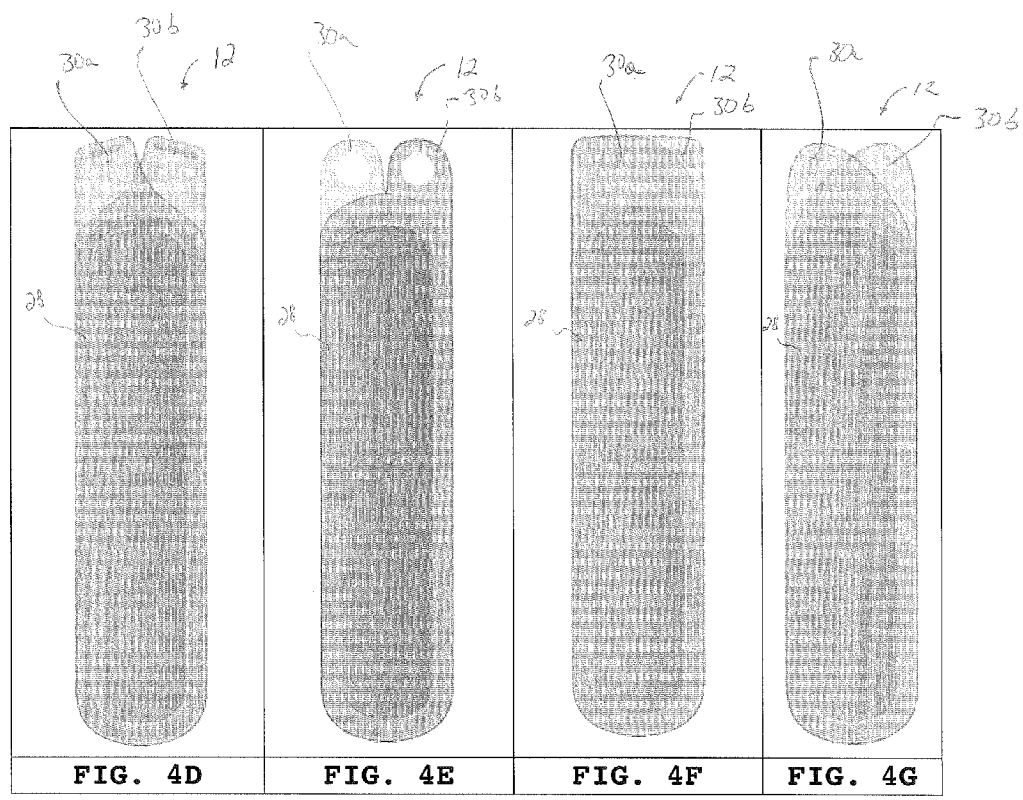

ORTHOPEDIC PACKAGING

CROSS-REFERENCE TO RELATED APPLICATIONS

The present application claims the benefit of the filing date of U.S. Provisional Patent Application No. 62/050,407 filed Sep. 15, 2014, the disclosure of which is hereby incorporated herein by reference.

BACKGROUND OF THE INVENTION

The present invention relates to packaging for orthopedic implants and instrumentation, such as screws, nails or the like.

Maintaining proper sterilization of implants and instruments utilized in orthopedic surgery is of the utmost importance. Implants and instruments that are improperly sterilized or maintained can lead to infections in a patient. These infections can have significant side effects, including some that may require additional surgery. As such, significant efforts are generally undertaken to sterilize and maintain sterilization of implants and instruments.

In many cases, sterilized implants and/or instruments are delivered to the surgical theater in packaging designed to maintain the sterilization. The packaging must be opened to allow for access to the components. This often requires manipulation of the packaging in a manner so that the implants or instruments are not subjected to contamination. For instance, traditional plastic packaging is often opened just enough so that the components contained therein can be dumped onto a tray, i.e., without grasping by hand. This not only makes the package opening more difficult and/or time consuming, but also puts the implants and/or instruments in a precarious situation where the potential for contamination is actually increased (e.g., inadvertent dropping of the component).

Therefore, there exists a need for an improved packaging construct that overcomes the shortcomings of the prior art.

BRIEF SUMMARY OF THE INVENTION

The present invention provides a packaging suitable for housing an orthopedic implant or instrument that prevents contamination of the orthopedic device by a user. The packaging is such that the user can grasp the packaging, while utilizing a tool or the like to engage the device. This improves upon prior packaging, which generally required the user to dump or other dispose of the device onto a surgical tray or the like. The packaging also includes a double barrier to potential contamination.

A first aspect of the present invention is a package for an orthopedic device having an inner packaging including first and second portions moveable from a first position to a second position and an outer packaging surrounding the inner packaging. The orthopedic device can be accessed upon removal of the outer packaging from the inner packaging and movement of the first and second portions to the second position.

In certain embodiments of the foregoing aspect, the outer packaging includes two portions sealed together, with or without two tabs associated with the two portions. The packaging may also include a spacer situated within the inner packaging. The first and second portions of the inner packaging may be connected to each other at a living hinge. The orthopedic device can be accessed by a tool while the first and second portions are in the second position. An orthopedic implant may be contained within the inner packaging. The implant may be any type of implant, including, but not limited to nails, screws or the like. The packaging may also be utilized to contain orthopedic instruments or the like.

Another aspect of the present invention is a method of removing an orthopedic device from a package. The method includes the steps of removing an outer packaging surrounding an inner packaging, moving a first portion of the inner packaging with respect to a second portion of the inner packaging to provide access to the orthopedic device and without directly contacting the orthopedic device by hand, removing the orthopedic device from the inner packaging.

In certain embodiments of the foregoing aspect, the method further includes the step of engaging the orthopedic device with a tool. The removing the orthopedic device step may be performed with the tool and while the user grasps the inner packaging. Removing the outer packing step may include peeling two portions away from one another. Like above, the orthopedic device may be an orthopedic implant, including nails, screws or the like. The orthopedic device may also be an orthopedic instrument.

Yet another aspect of the present invention is another package for an orthopedic device including an inner packaging and an outer packaging. The inner packaging includes first and second portions moveable between a first position and a second position, a spacer. The outer packaging surrounds the inner packaging, so that the orthopedic device can be accessed upon removal of the outer packaging from the inner packaging and movement of the first and second portions to the second position.

Other embodiments of this additional aspect may include an outer packaging that includes two portions sealed together and two tabs associated with the two portions. The first and second portions may be connected to each other at a living hinge. The orthopedic device may be accessed by a tool while the first and second portions are in the second position. The packaging may further include an orthopedic implant contained within the inner packaging.

BRIEF DESCRIPTION OF THE DRAWINGS

A more complete appreciation of the subject matter of the present invention and of the various advantages thereof can be realized by reference of the following detailed description in which reference is made to the accompanying drawings in which:

FIGS. 4A-G are views of different outer packaging constructs that can be utilized in the packaging of FIG. 1.

DETAILED DESCRIPTION

Figure 1:
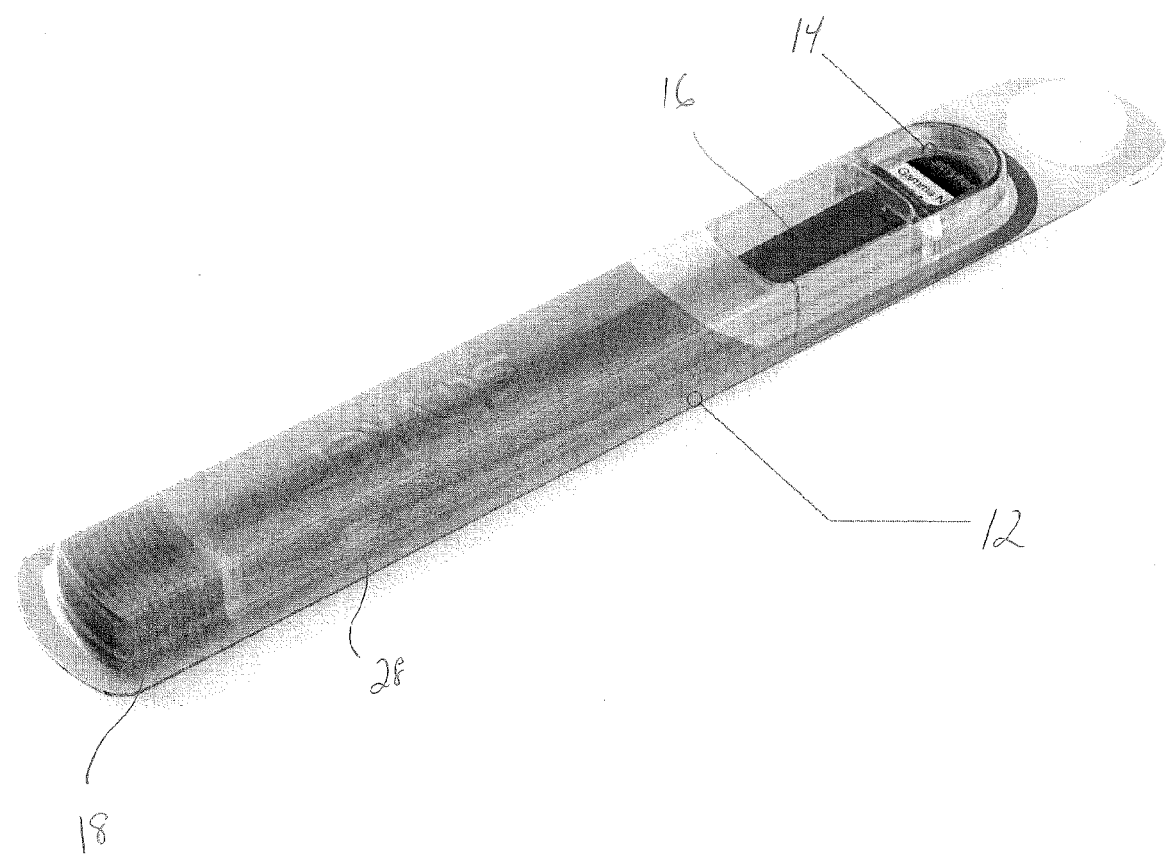
FIG. 1 is a perspective view of an implant packaging according to one embodiment of the present invention.

FIG. 1 depicts an implant packaging 10. Although shown housing an orthopedic nail, it is to be understood that package 10 may be sized and/or shaped to house any type of orthopedic implant or instrument. For instance, it is contemplated to configure packaging 10 to house a knee implant, hip implant, spinal implant, orthopedic screw, or the like. Likewise, although shown as being constructed of a translucent material, packaging 10 may be constructed of entirely clear and/or opaque materials. As shown, package 10 includes an outer packaging 12, an inner packaging 14, an implant 16 and a spacer 18.

Figure 2:
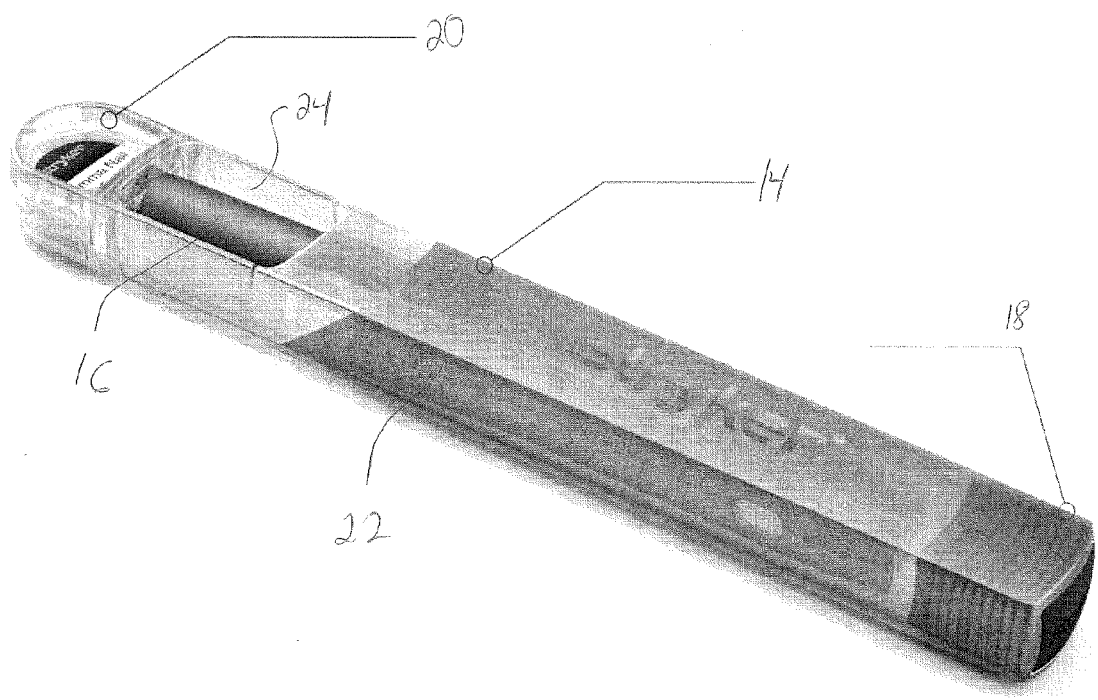
FIG. 2 is a perspective view of the inner packaging of the implant packaging of FIG. 1.
Figure 3:
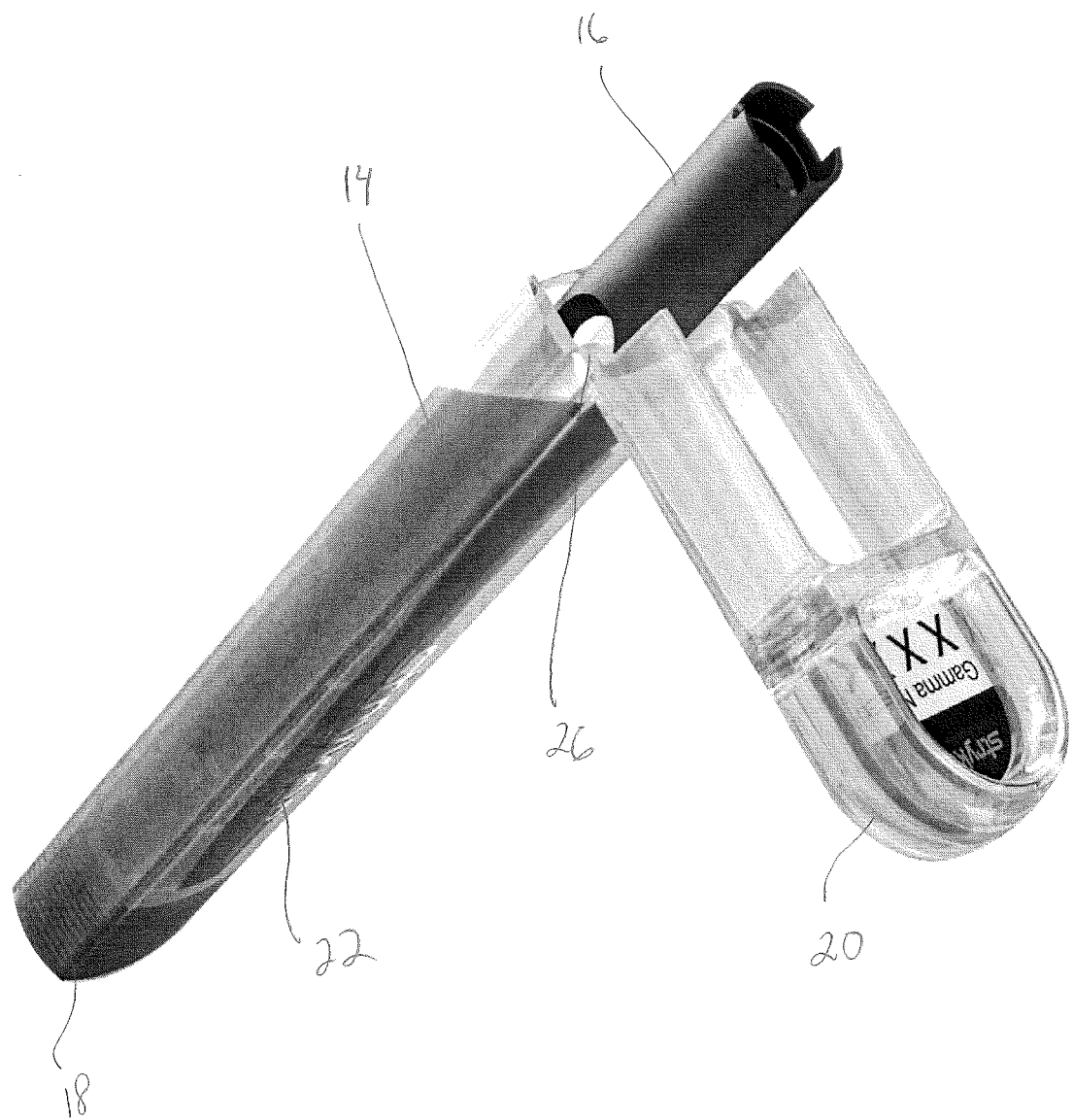
FIG. 3 is another perspective view of the inner packaging of FIG. 2 in a position in which the implant can be removed therefrom.
Figures 4A, 4B, 4C:
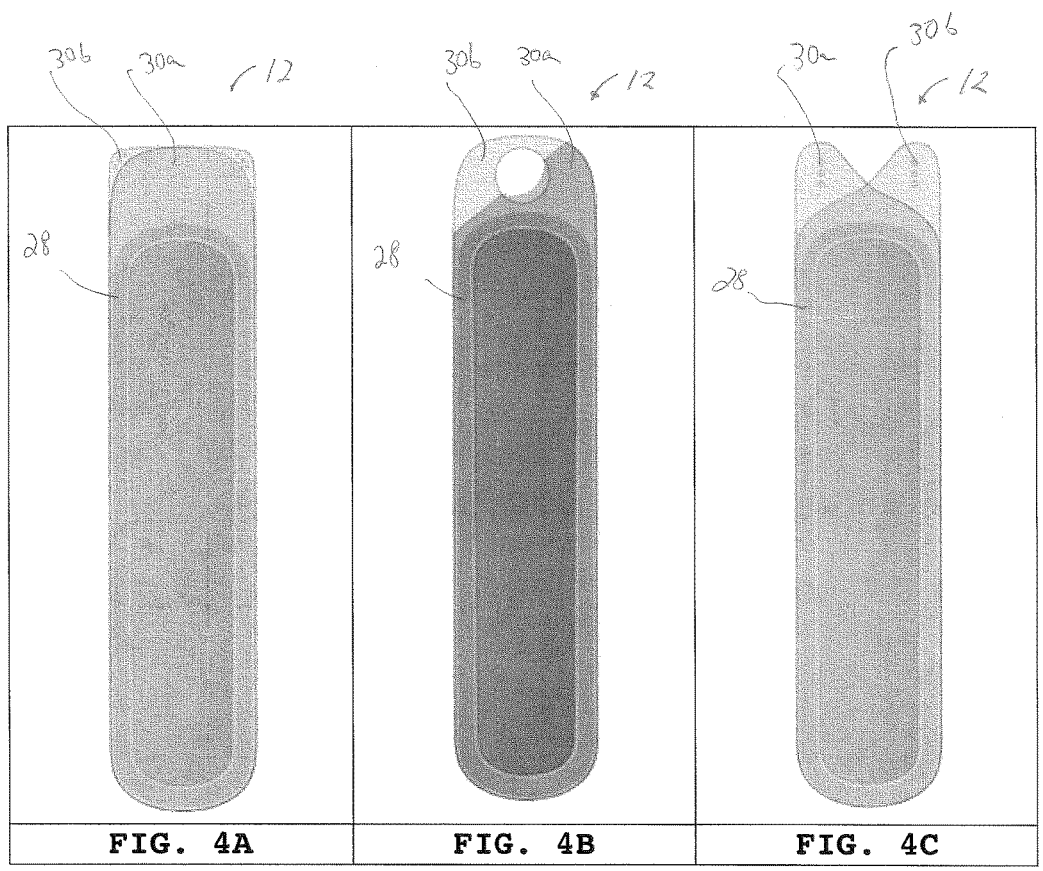

FIG. 2 depicts package 10 with outer packaging 12 having been removed therefrom. Inner packaging 14 includes a cap portion 20, a container portion 22 and a window 24. Cap portion 20 is connected to container portion 22 via a living hinge 26 (best shown in FIG. 3). This design allows for implant 16 to be fully accessible upon rotation of cap portion 20 with respect to container portion 22. It is contemplated that living hinge 26 could be replaced with a standard hinge or any other structure suitable to allow for the above-discussed rotation. In certain embodiments, living hinge 26 or any other structure may be designed to allow for multiple uses of inner packaging (i.e., cap portion 20 can be rotated back into the position of FIGS. 1 and 2). Alternatively, living hinge 26 could be designed to allow for a single use, and in fact alert a user that such use has already occurred.

FIGS. 4A-G show several different configurations that outer packaging 12 may exhibit. Consistent with each design is the fact that outer packaging 12 is constructed of at least two different portions attached to each other along a sealed seam 28. These portions are preferably formed of flexible materials that allow for the manipulation ultimately required for their removal from package 10 (discussed below). Preferably, sealed seam 28 extends entirely around portions of the two portions that encompass inner packaging 14. Additionally, outer packaging 12 includes two graspable tabs 30a and 30b that allow for the two portions of the outer packaging to be peeled away from each other at seam 28. This necessarily allows for inner packaging 14 to be accessed. As shown in FIGS. 4A-G, the tabs may be of many different configurations, with each being facilitating the peeling step noted above. Likewise, it is to be understood that while FIGS. 4A-G illustrate an outer packaging 12 of a particular shape and size, such can be modified in order to accommodate differently shaped and sized inner packaging 14. Like inner packaging 14, outer packaging 12 is shown as being translucent, but may be constructed of entirely clear and/or opaque materials.

Figure 5:
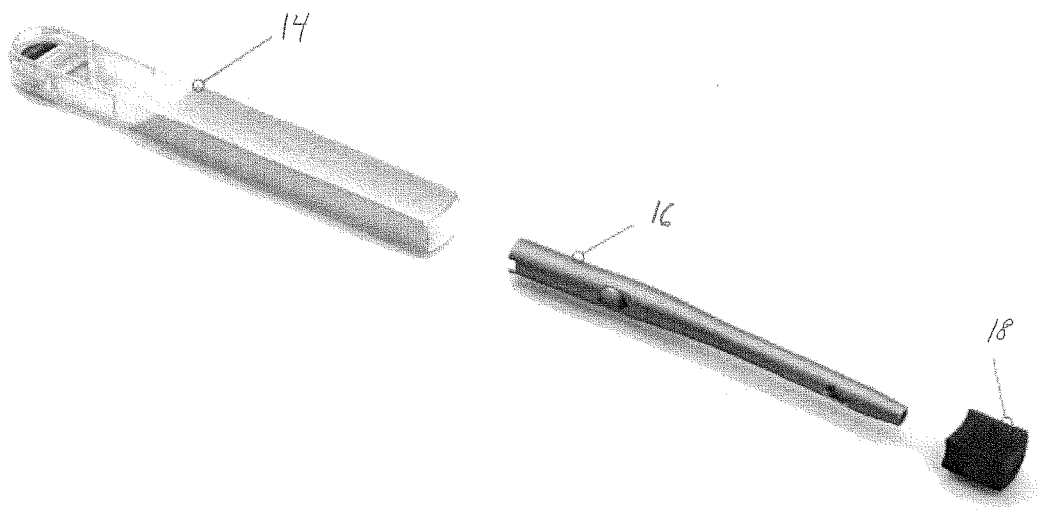
FIG. 5 is a perspective exploded view of the inner packaging and implant of FIG. 2.
Figure 6:
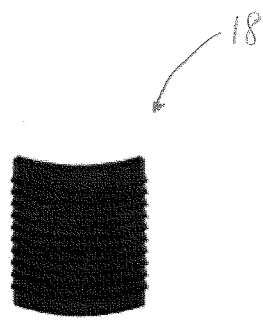
FIG. 6 is a perspective view of a spacer included in the inner packaging of FIG. 2.

FIG. 5 shows implant 16 (in the form of a nail) removed from inner packaging 14. Moreover, spacer 18 is shown removed from inner packaging 14 in that same figure, as well as in further detail in FIG. 6. The inclusion of spacer 18 allows for inner packaging 14 to accommodate differently sized and/or shaped implants. For instance, implant (nail) 16 may be provided in various lengths for use in surgeries of patients of different sizes. By utilizing differently sized spacers 18, several or all of the various length implants can be securely fit within inner packaging 14. Shorter nails would require larger spacers 18, while longer nails would require smaller spacers 18. As is best shown in FIG. 6, spacer 18 is essentially a body designed to be slid into inner packaging 14 and ultimately disposed at a bottom end thereof. Although shown as being a solid construct, it is contemplated to form spacer 18 out of a plurality of individually and/or interconnected elements. This would allow for the variability of the spacer to accommodate differently sized implants.

Package 10 may be utilized as follows. First, subsequent to manufacturing of implant 16, a suitably sized and shaped inner packaging 14 may be selected along with a suitably sized spacer 18 for maintaining the implant within the packaging in a somewhat fixed manner. Implant 16 may then be sterilized utilizing any known method. Portions 20 and 22 may be oriented to allow for insertion of the implant within inner packaging 14. Those portions may then be situated in the position shown in FIGS. 1 and 2. Outer packaging 12 can thereafter be placed and sealed around inner packaging 14. This process may be achieved by any known method for sealing.

Package 10 may thereafter be delivered to the surgical theater, where it must be opened in order for implant 16 to be utilized. First, tabs 30a and 30b are grasped by a user and the portions of outer packaging 12 are peeled away from one another. These portions may be discarded after removal from inner packaging 14. Portion 20 is then rotated with respect to portion 22 to place inner packaging 14 in a position where implant 16 is accessible. The user, while only grasping inner packaging 14 may remove implant 16 therefrom, preferably with a tool or the like so that the implant is never actually directly touched by the user. Implant 16 can then be implanted in the body of the patient without ever having been subjected to potential contamination.

Figure 7:
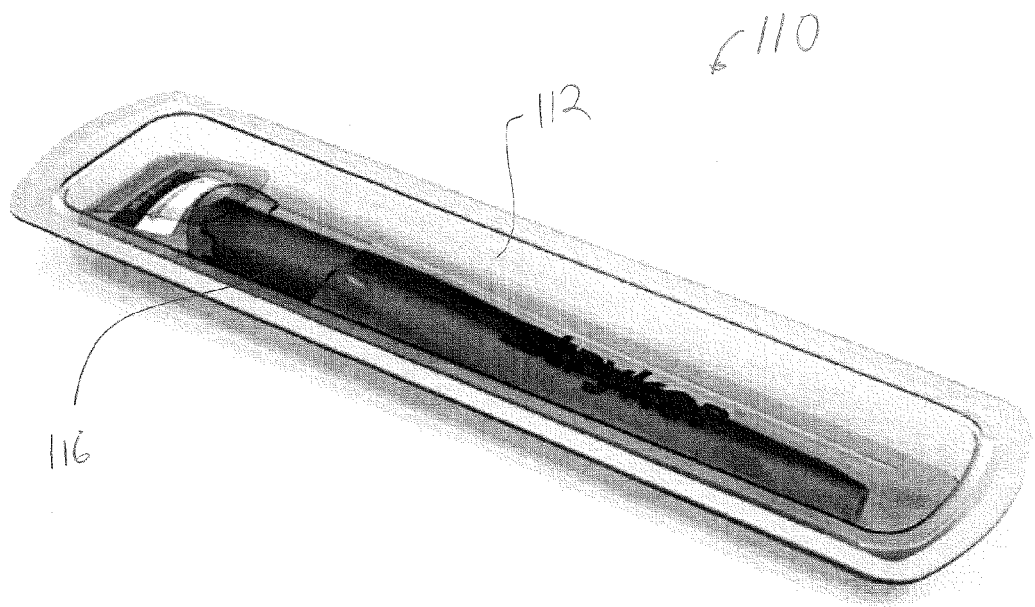
FIG. 7 is a perspective view of an implant packaging according to another embodiment of the present invention.
Figure 8:
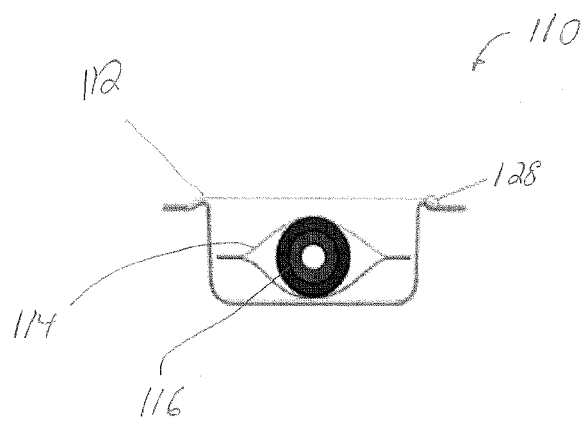
FIG. 8 is a cross-sectional view of the implant packaging of FIG. 7.
Figure 9:
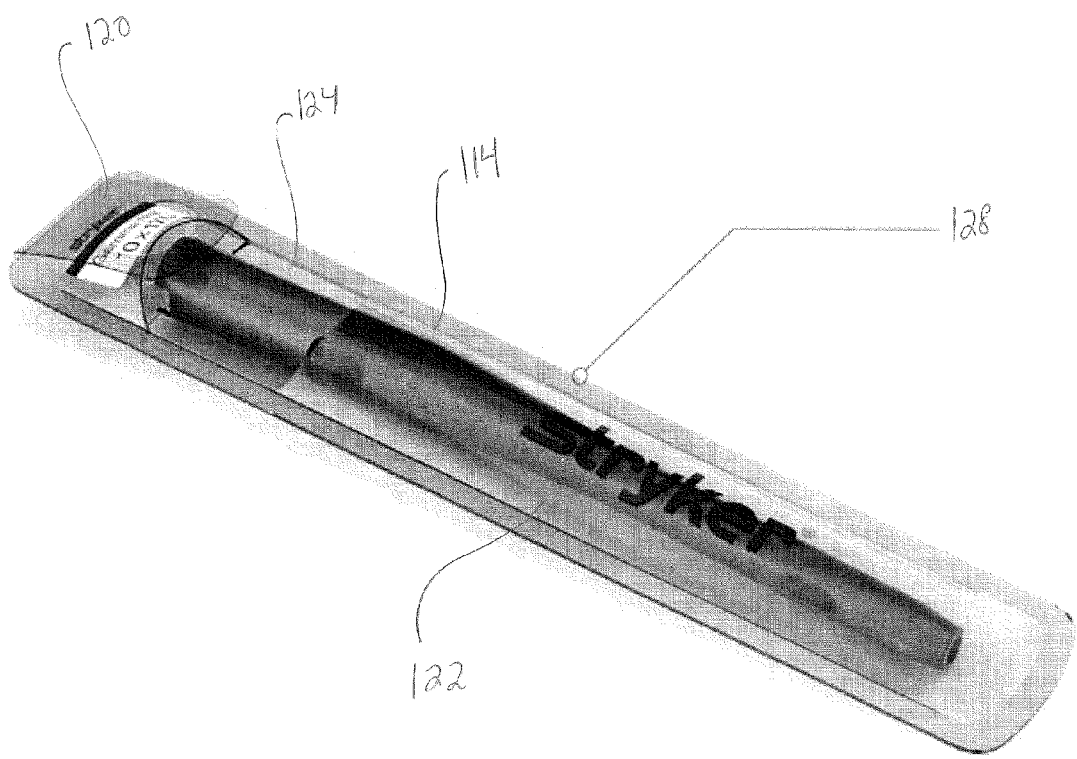
FIG. 9 is a perspective view of the inner packaging of the implant packaging of FIG. 7.

FIGS. 7-9 depict another embodiment package 110 in accordance with the present invention. Because of the similarities of packages 10 and 110, like reference numerals are utilized for the latter, but within the 100-series of numbers. For instance, package 110 includes outer packaging 112, inner packaging 114 and implant 116. Package 110 is largely utilized in the same fashion as package 10 is, but a spacer or the like is not utilized. This is largely due to the more flexible construction of inner packaging 114, which can contain differently sized implants 116 in a somewhat fixed without the need for a spacer.

Figure 10:
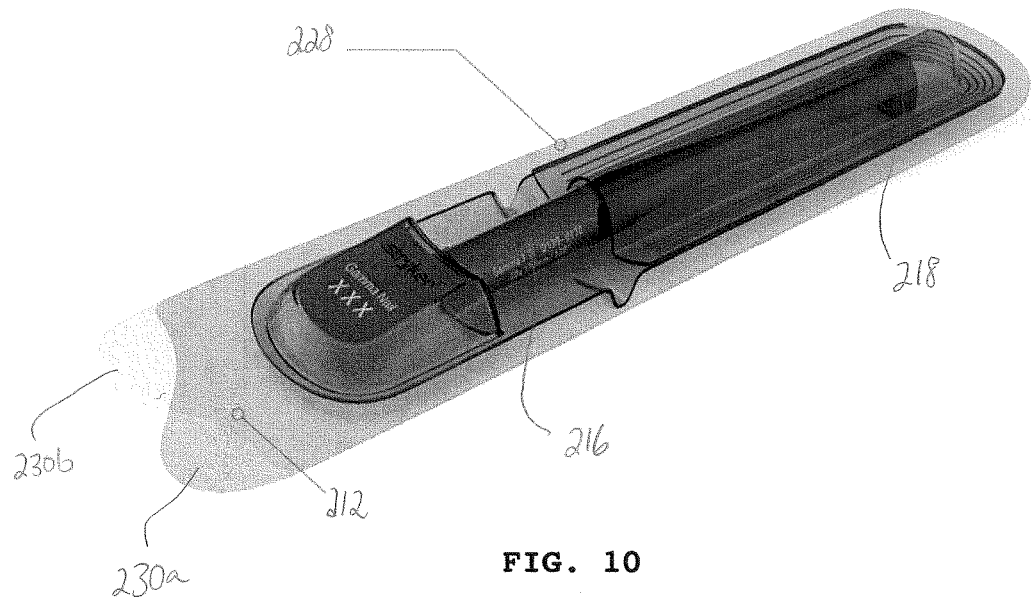
FIG. 10 is a perspective view of an implant packaging according to another embodiment of the present invention.
Figure 11:
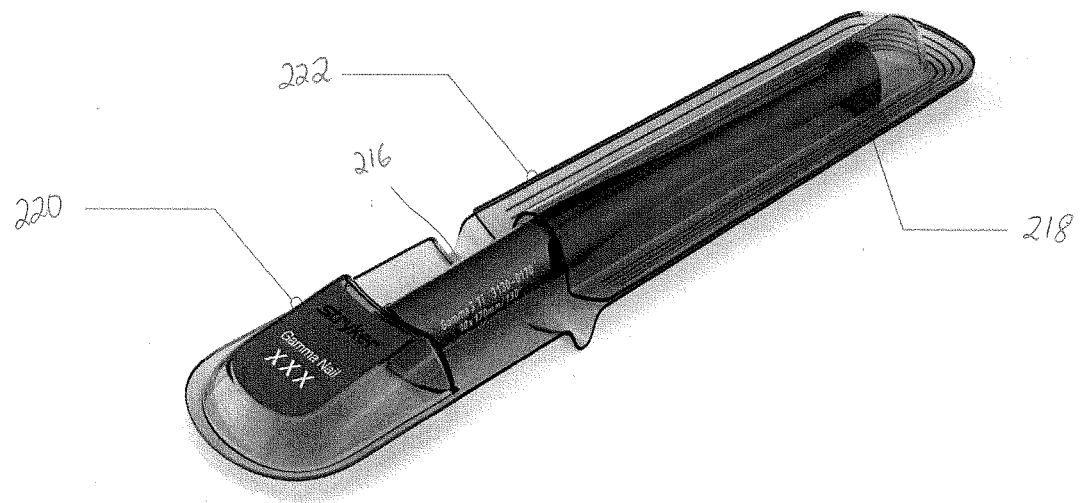
FIG. 11 is a perspective view of the inner packaging of the implant packaging of FIG. 10.
Figure 12:
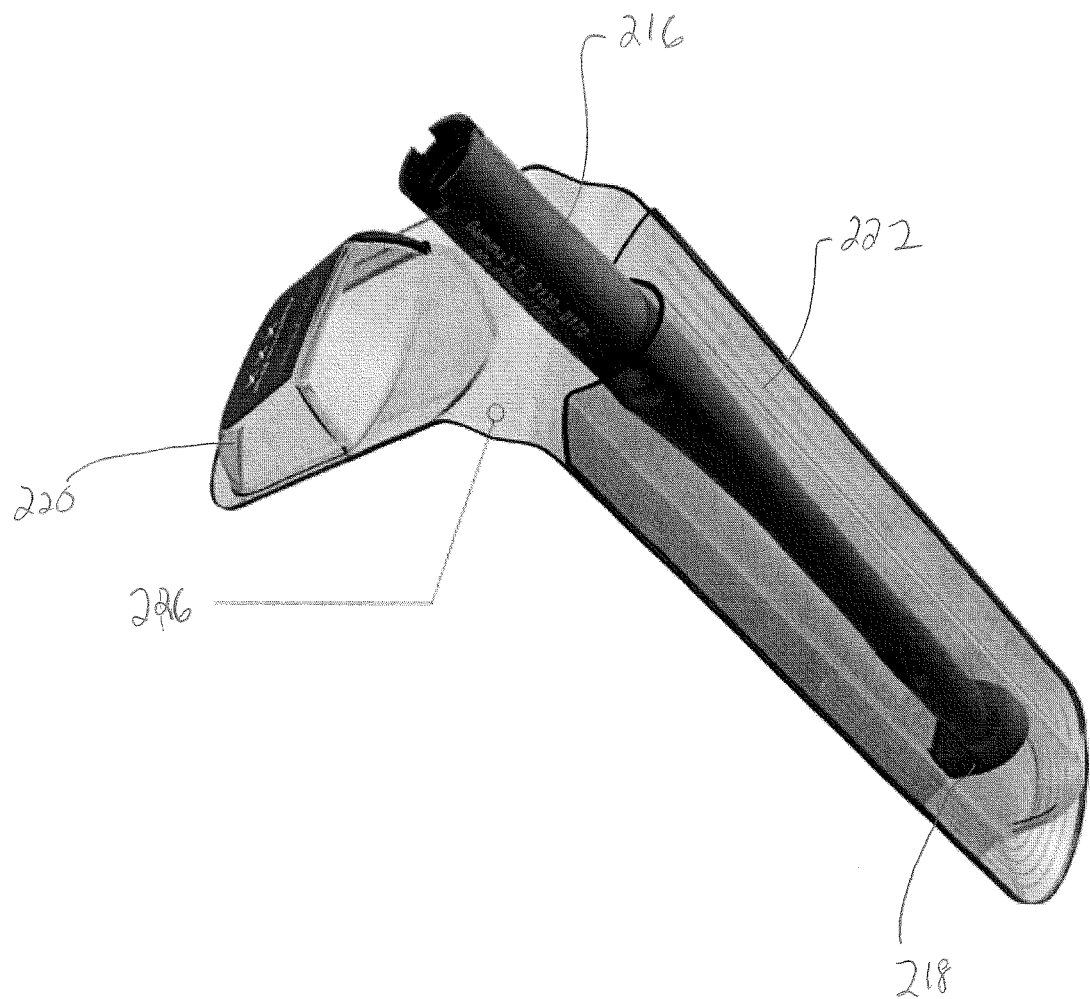
FIG. 12 is another perspective view of the inner packaging of FIG. 11 in a position in which the implant can be removed therefrom.

Similarly, package 210 of FIGS. 10-12 is of a similar design to packages 10 and 110. Again, like reference numerals within the 200-series are utilized. However, unlike package 110, package 210 does utilize a spacer 218. This spacer is somewhat different than above-discussed spacer 18 in that it does not extend entirely to the bottom end of inner packaging 214. Rather, spacer 218 may be affixed within inner packaging 214 at different positions depending upon the size and/or shape of implant 216.

Figure 13:
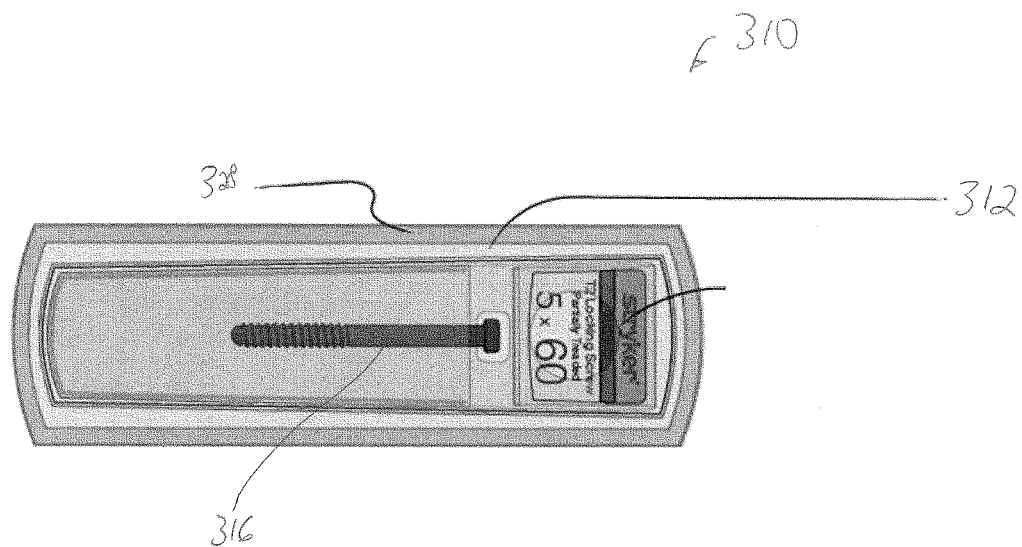
FIG. 13 is a perspective view of an implant packaging according to another embodiment of the present invention.
Figure 14:
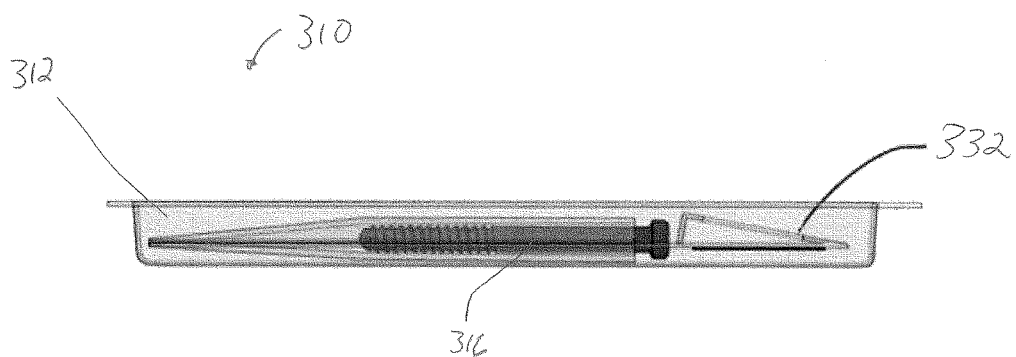
FIG. 14 is a side view of the implant packaging of FIG. 13.
Figure 15A:
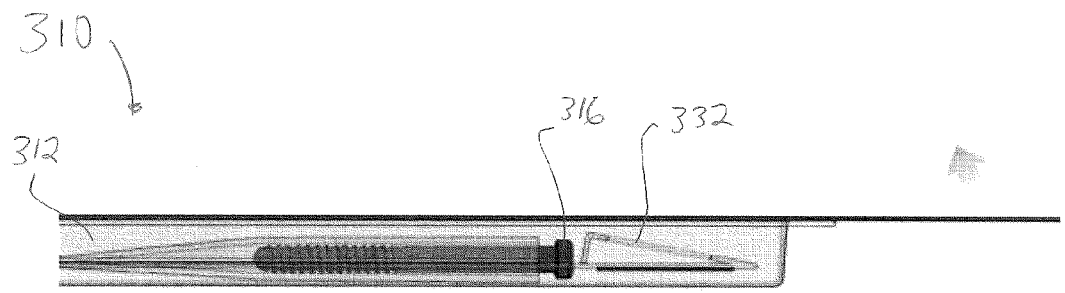
FIGS. 15A-15D are views illustrating access of a screw from the implant packaging of FIG. 13.
Figure 15B:
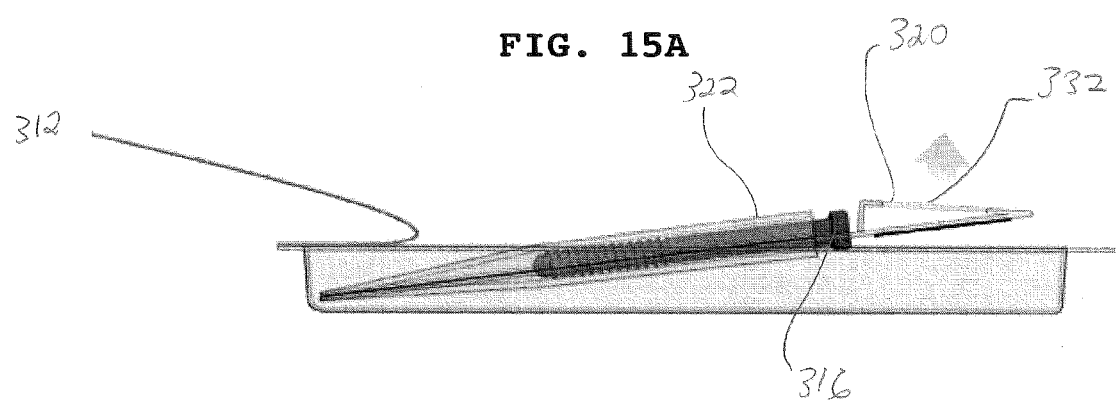
Figure 15C:
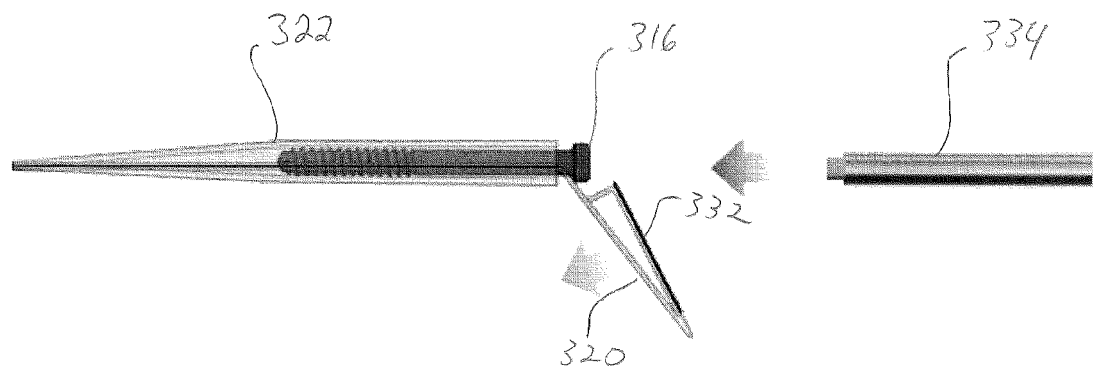
Figure 15D:
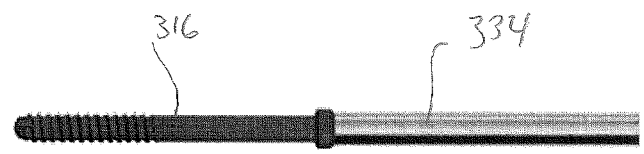

Package 310 is shown in FIGS. 13 and 14 as being a screw 316 holding device that, like the above packages, includes an outer packaging 312 and an inner packaging 314. Much like inner packaging 114, inner packaging 314 is of a flexible material that holds screw 316 without the need for a spacer or the like. While inner packaging 314 includes portions 320 and 322 and operates like the foregoing inner packaging, it also includes a member 332 that aids in the rotation of the portions with respect to one another. As shown in FIGS. 15A-15D, packaging 310 is used in much the same way as is described above. Ultimately, a screw driver 334 is engaged with screw 316 without the screw ever having been subjected to direct contact, and potential contamination from a user.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A package for an orthopedic device comprising:
an inner packaging including first and second portions, the first and second portions moveable from a first position to a second position and connected to one another in both the first and second positions, wherein the first and second portions extend in opposite directions from the connection between them when in the first position and one of the first and second portions includes a window as an opening such that when the orthopedic device is inside the package, the orthopedic device is exposed though the opening; and
an outer packaging surrounding the inner packaging,
wherein the orthopedic device can be accessed upon removal of the outer packaging from the inner packaging and movement of the first and second portions to the second position.

2. The package of claim 1, wherein the outer packaging includes two portions sealed together.

3. The package of claim 2, wherein the outer packaging further includes two tabs associated with the two portions.

4. The package of claim 1, further comprising a spacer situated within the inner packaging.

5. The package of claim 1, wherein the first and second portions are connected to each other at a living hinge.

6. The package of claim 1, wherein the orthopedic device can be accessed by a tool while the first and second portions are in the second position.

7. The package of claim 1, further comprising an orthopedic implant contained within the inner packaging.

8. A method of removing an orthopedic device from within a package comprising the steps of:
removing an outer packaging surrounding an inner packaging of the package, wherein the orthopedic device is disposed within the inner packaging;
moving a first portion of the inner packaging with respect to a second portion of the inner packaging connected to the first portion to provide access to the orthopedic device, and first and second portions extending in opposite directions from the connection between them prior to moving the first portion with respect to the second portion; and
without directly contacting the orthopedic device by hand, removing the orthopedic device from the inner packaging, wherein the orthopedic device disposed within the inner packaging is exposed through a window in one of the first and second portions prior to moving the first portion of the inner packaging with respect to the second portion.

9. The method of claim 8, further comprising the step of engaging the orthopedic device with a tool.

10. The method of claim 9, wherein the removing the orthopedic device step is performed with the tool and while the user grasps the inner packaging.

11. The method of claim 8, wherein the removing the outer packing step includes peeling two portions away from one another.

12. The method of claim 8, wherein the orthopedic device is an orthopedic implant.

13. A package for an orthopedic device comprising:
an inner packaging including:
first and second portions moveable between a first position and a second position and connected to one another in both the first and second positions, wherein the first and second portions extend in opposite directions from the connection between them when in the first position, and one of the first and second portions includes a window as an opening such that when the orthopedic device is inside the package, the orthopedic device is exposed through the opening; and
a spacer, and
an outer packaging surrounding the inner packaging,
wherein the orthopedic device can be accessed upon removal of the outer packaging from the inner packaging and movement of the first and second portions to the second position.

14. The package of claim 13, wherein the outer packaging includes two portions sealed together and two tabs associated with the two portions.

15. The package of claim 13, wherein the first and second portions are connected to each other at a living hinge.

16. The package of claim 13, wherein the orthopedic device can be accessed by a tool while the first and second portions are in the second position.

17. The package of claim 13, further comprising an orthopedic implant contained within the inner packaging.

* * * * *